(12) United States Patent
Gergely et al.

(10) Patent No.: US 11,224,604 B2
(45) Date of Patent: Jan. 18, 2022

(54) TREATMENT OF GRAFT VERSUS HOST DISEASE IN TRANSPLANT PATIENTS

(71) Applicant: PRIOTHERA LIMITED, Dublin (IE)

(72) Inventors: Peter Gergely, Oberwil (CH); Kazuhiko Kuriyama, Nogi-machi (JP)

(73) Assignee: PRIOTHERA LIMITED, Dublin (IE)

( * ) Notice: Subject to any disclaimer, the term of this patent is extended or adjusted under 35 U.S.C. 154(b) by 328 days.

(21) Appl. No.: 15/882,392

(22) Filed: Jan. 29, 2018

(65) Prior Publication Data

US 2018/0153911 A1 Jun. 7, 2018

Related U.S. Application Data

(63) Continuation of application No. 14/768,744, filed as application No. PCT/IB2014/059067 on Feb. 18, 2014, now abandoned.

(60) Provisional application No. 61/766,830, filed on Feb. 20, 2013.

(51) Int. Cl.

| | |
|---|---|
| *A61K 31/661* | (2006.01) |
| *A61K 38/13* | (2006.01) |
| *A61K 31/137* | (2006.01) |
| *A61K 31/255* | (2006.01) |
| *A61K 31/519* | (2006.01) |
| *A61K 31/675* | (2006.01) |
| *A61K 31/7076* | (2006.01) |
| *A61K 35/28* | (2015.01) |
| *A61K 35/34* | (2015.01) |
| *A01B 1/02* | (2006.01) |
| *A61K 31/145* | (2006.01) |
| *A61K 31/664* | (2006.01) |
| *A61N 5/10* | (2006.01) |
| *C07C 323/32* | (2006.01) |
| *C07F 9/09* | (2006.01) |
| *A61K 35/12* | (2015.01) |

(52) U.S. Cl.
CPC ............. *A61K 31/661* (2013.01); *A01B 1/02* (2013.01); *A61K 31/137* (2013.01); *A61K 31/145* (2013.01); *A61K 31/255* (2013.01); *A61K 31/519* (2013.01); *A61K 31/664* (2013.01); *A61K 31/675* (2013.01); *A61K 31/7076* (2013.01); *A61K 35/28* (2013.01); *A61K 35/34* (2013.01); *A61K 38/13* (2013.01); *A61N 5/10* (2013.01); *C07C 323/32* (2013.01); *C07F 9/094* (2013.01); *A61K 2035/122* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 6,383,481 B1 | 5/2002 | Ikehara et al. | |
| 6,960,692 B2 | 11/2005 | Kohno | |
| 7,482,491 B2 | 1/2009 | Kohno | |
| 7,763,752 B2 | 7/2010 | Kohno | |
| 7,781,617 B2 * | 8/2010 | Kudou | A61P 19/04 564/336 |
| 7,807,854 B2 | 10/2010 | Kudou et al. | |
| 2010/0099606 A1 | 4/2010 | Kudou et al. | |

FOREIGN PATENT DOCUMENTS

| | | |
|---|---|---|
| JP | H11343242 A | 12/1999 |
| WO | 98/20932 A2 | 5/1998 |
| WO | WO 2006/009092 A1 | 1/2006 |
| WO | WO 2006/073126 A1 | 7/2006 |
| WO | WO2011/138398 A1 | 11/2011 |
| WO | WO2011/140170 A1 | 11/2011 |

OTHER PUBLICATIONS

Jagasia et al, Transplantation 2012, 119(1):296-307. (Year: 2012).*
Lee et al, Transplantation, 2003, 76(8): 1155-1158. (Year: 2003).*
Kim et al, J Clin Invest, 2003, 111(5):659-669. (Year: 2003).*
Fujishiro, J., et al., Use of Sphingosine-1-Phosphate 1 Receptor Agonist, KRP-203, in Combination with a Subtherapeutic Dose of Cyclosporine A for Rat Renal Transplantation, Transplantation, Sep. 27, 2006, pp. 804-812, vol. 82, No. 6.
Shimizu, H., et al. KRP203, a Novel Synthetic Immunosuppressant, Prolongs Graft Survival and Attenuates Chronic Rejection in Rat Skin and Heart Allografts, Circulation, 2005, pp. 222-229 vol. 111.
Taylor, P.A. et al., Insights into the mechanism of FTY720 and compatibility with regulatory T cells for the inhibition of graft-versus-host disease (GVHD). Blood, Nov. 1, 2007, pp. 3480-3488, vol. 110, No. 9.
Miller et al. Bone Marrow Transplantation, 2004, vol. 33, pp. 881-889.
U.S. Appl. No. 15/297,683; Gergely et al. filed Oct. 19, 2016.
U.S. Appl. No. 14/341,891, Gergely et al. filed Jul. 28, 2014.
Appelbaum, "Optimising the conditioning regimen for acute meyloid leukaemia" Best Practice & Research Clinical Haematology, 2009, vol. 22, pp. 543-550.
Harada et al., "Hematopoietic Stem Cell Transplantation for Refractory Malignant Tumors and Autoimmune Diseases", Fukuoka Acta Medica (Fukuoka Igeku Zasshi), (2006), vol. 97, No. 7, p. 220-222 (English Translation).
Gupta et al., "Salts of Therapeutic Agents: Chemical, Physicochemical, and Biological Considerations,"*Molecules*, vol. 23, No. 1719, 15 pages (2018).

* cited by examiner

*Primary Examiner* — Allison M Fox
(74) *Attorney, Agent, or Firm* — Hoxie & Associates LLC

(57) ABSTRACT

The present invention relates to a method of treating patients who undergo hematopoietic stem cell transplantation (HSCT) with peripheral blood mobilized stem cells for hematological malignancies and for whom the risk for severe acute graft versus host disease (GVHD) is considerable.

16 Claims, No Drawings

TREATMENT OF GRAFT VERSUS HOST DISEASE IN TRANSPLANT PATIENTS

The present invention relates to a method of treating patients who undergo hematopoietic stem cell transplantation (HSCT) with peripheral blood mobilized stem cells for hematological malignancies and for whom the risk for severe acute graft versus host disease (GVHD) is considerable.

BACKGROUND

Acute graft-versus-host disease (GVHD) may occur after allogeneic hematopoietic stem cell transplant and is usually a reaction of donor immune cells against host tissues. Activated donor T cells typically damage host epithelial cells after an inflammatory cascade that begins with the preparative regimen. Statistically, about 35%-50% of hematopoietic stem cell transplant (HSCT) recipients/patients may develop acute GVHD. The exact risk is usually dependent on the stem cell source, age of the patient, conditioning, and GVHD prophylaxis/treatment used.

Patients usually may have involvement of three organs such as skin (rash/dermatitis), liver (hepatitis/jaundice), and gastrointestinal tract (abdominal pain/diarrhea).

Acute GVHD is typically staged and graded (grade 0-IV) by the number and extent of organ involvement. Patients with grade III/IV acute GVHD tend to have a poor outcome (life threatening). Generally a patient may be treated by optimizing the immunosuppression and for example by adding methylprednisolone. About 50% of patients may have a solid response to methylprednisolone. If patients progress after 3 days or are not improved after 7 days, they will get salvage (second-line) immunosuppressive therapy for which there is unfortunately no standard-of-care therapy.

Therefore there is a high unmet medical need to have further pharmaceutically effective drugs for preventing and/or treating GVHD.

In an embodiment the present invention relates to a method of treating and/or preventing GVHD in a patient undergoing HSCT, which method comprises:

1. Administering to the patient an effective amount of a compound of formula (I) or a pharmaceutically acceptable salt thereof;
2. Conditioning said patient thereby destroying substantially the bone marrow and immune system wherein said conditioning includes treatment of said patient with an effective amount of a chemotherapeutic agent such as cyclophosphamide and/or by treating said patient with a high-dose chemoradiation therapy; and
3. Transplanting hematopoietic stem cells from a donor to said patient.

In a method as described above, a compound of formula (I) or a pharmaceutically acceptable salt thereof is,

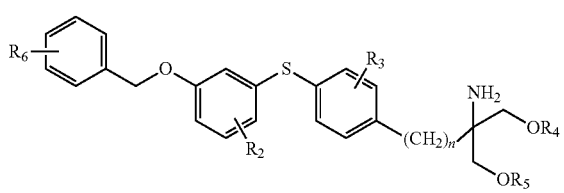

(I)

wherein $R_2$ is H, halogen, trihalomethyl, $C_{1-4}$alkoxy: $C_{1-7}$alkyl, phenethyl or benzyloxy;

$R_3$ H, halogen, $CF_3$, OH, $C_{1-7}$alkyl, $C_{1-4}$alkoxy, benzyloxy, phenyl or $C_{1-4}$alkoxymethyl;

each of $R_4$ and $R_5$, independently is H or a residue of formula (a)

(a)

wherein each of $R_8$ and $R_9$, independently, is H or $C_{1-4}$alkyl optionally substituted by halogen:

and n is an integer from 1 to 4; and $R_6$ is hydrogen, halogen, $C_{1-7}$alkyl, $C_{1-4}$alkoxy or trifluoromethyl.

In another embodiment the invention relates to a method of treating and/or preventing GVHD in patient undergoing HSCT, wherein in the compound of formula (I) or a pharmaceutically acceptable salt thereof $R_3$ is chlorine, and wherein the remaining variables are as defined above. In another embodiment the invention relates to a method of treating and/or preventing GVHD in patient undergoing HSC, wherein in the compound of formula (I) or a pharmaceutically acceptable salt thereof $R_2$ is H, $R_3$ is chlorine, and $R_6$ is hydrogen, and wherein the remaining variables are as defined above.

In another embodiment the invention relates to a method of treating and/or preventing GVHD in patient undergoing HSCT, wherein in the compound of formula (I) or a pharmaceutically acceptable salt thereof $R_2$ is H, $R_3$ is chlorine, $R_6$ is hydrogen, each of $R_4$ and $R_5$, independently is H or a residue of formula (a)

(a)

and wherein each of $R_8$ and $R_9$ is H, and wherein the remaining variables are as defined above.

In another embodiment the invention relates to a method of treating and/or preventing GVHD in patient undergoing HSCT, wherein the compound of formula (I) or a pharmaceutically acceptable salt thereof is a compound of formula (II).

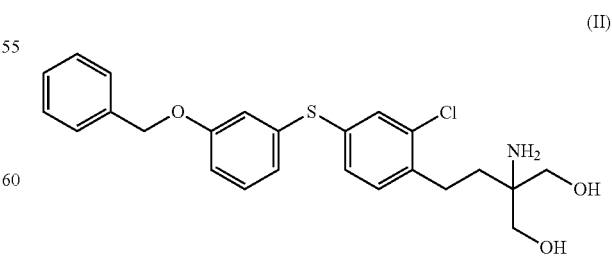

(II)

or a pharmaceutically acceptable salt thereof, or or a phosphate derivative thereof of the following formulae (IIa), (IIb):

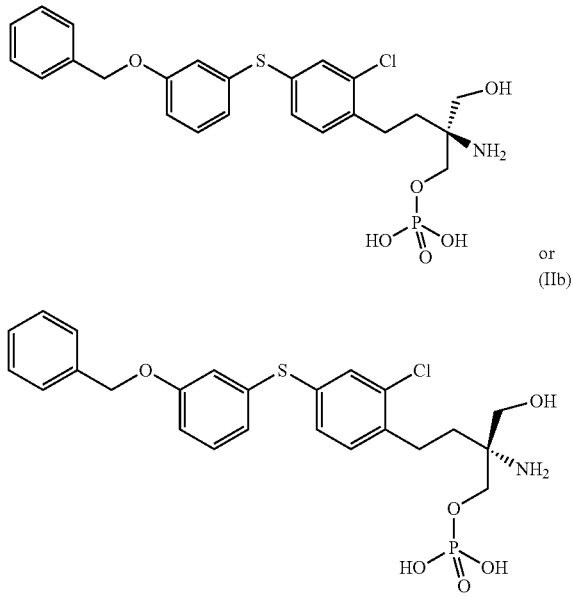

or a pharmaceutically acceptable salt thereof.

In another embodiment the invention relates to a method of treating and/or preventing GVHD in patient undergoing HSCT, wherein the compound of formula (I) or a pharmaceutically acceptable salt thereof 2-amino-2-[4-(3-benzyloxyphenylthio)-2-chlorophenyl]ethyl-propane-1,3-diol.

In another embodiment the invention relates to a compound of formula (I) or a pharmaceutically acceptable salt thereof in the use in the treatment and/or prevention of GVHD in a patient who was first conditioned as described above and who then received a hematopoietic stem cell transplantation (HSCT) from a donor.

As used herein 2-amino-2-[4-(3-benzyloxyphenylthio)-2-chlorophenyl]ethyl-propane-1,3-diol and/or its hydrochloride salt may also be referred to as KRP203.

As used herein, the term "halogen" or "halo" refers to fluoro, chloro, bromo, and iodo.

As used herein, the term "alkyl" refers to a fully saturated branched or unbranched hydrocarbon moiety having from 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, and the like, A substituted alkyl is an alkyl group containing one or more, such as one, two or three substituents selected from halogen, hydroxy or alkoxy groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have 1-7, or 1-4 carbon atoms.

A substituted alkoxy is an alkoxy group containing one or more, such as one, two or three substituents selected from halogen, hydroxy or alkoxy groups.

The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base sails by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrohromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Ma, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985): and in "Handbook of Pharmaceutical Salts; Properties, Selection, and Use" by Stahl and Wermuth (Wiley-VCH, Weinheirn, Germany, 2002).

As used herein the term "conditioning" or "conditioned" in the context of a patient pretreatment in need of HSCT typically means destroying substantially the bone marrow and immune system by a suitable procedure such as:

Reduced intensity conditioning (RIC) or myeloablative conditioning, e.g. Mini-Seattle Conditioning, e g. fludarabin or another chemotherapeutic agent typically at 30 mg/m3/day for three days followed by total body irradiation (TBI) typically at 1×200 cGy/day;

or

Myeloablative Conditioning, e.g. high dose chemotherapy and total body irradiation (TBI) is typically performed according to national guidelines adapted to institutional practices, and includes the administration of fludarabin, busulphan, methotrexate, cyclosporin A and cyclophosphamide. The following dosing regimens are given as examples:

1) Fludarabin at 25 mg/ml/day i.v.×3 days (for approximately 2-3 days) for a total dose of 75 mg/m2.

2) Busulphan at 0.8 mg/kg/8 h (for approximately 2 to 4 days)

3) Cyclophosphamide at 60 mg/kg/day i.v.×2 days (approximately for 2 days) for a total dose of 120 mg/kg. To reduce the risk of CYC-induced hemorrhagic cystitis, patients will also receive high volume fluid flushes and mesna.

4) TBI will occur from approximately days 8 to 10 (days −8 and −1 relative to HSCT).

The recommended TBI dose is 200 cGy given twice daily for a total dose of 1200 cGy.

SUMMARY OF THE INVENTION

Embodiment 1 describes a method of treating and/or preventing graft versos host disease (GVHD) in a patient undergoing hematopoietic stem cell transplantation (HSCT), which method comprises:

(i) Administering to the patient an effective amount of a compound of formula (I) or a pharmaceutical acceptable salt thereof;

(ii) Conditioning said patient thereby destroying substantially all bone marrow and the immune system; and (iii) Transplanting hematopoietic stem cells from a donor to said patient;

wherein said compound of formula (I) or a pharmaceutically acceptable salt thereof is

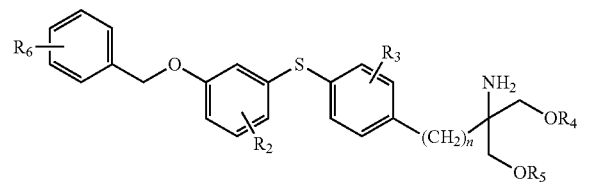

(I)

wherein $R_2$ is H, halogen, trihalomethyl, $C_{1-4}$alkoxy, $C_{1-2}$alkyl, phenethyl or benzyloxy;

$R_3$ H, halogen, $CF_3$, OH, $C_{1-2}$alkyl, $C_{1-4}$alkoxy, hemyloxy, phenyl or $C_{1-4}$alkoxymethyl;

each of $R_4$ and $R_5$, independently is H or a residue of formula (a)

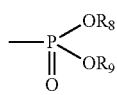

(a)

wherein each of $R_8$ and $R_9$, independently, is H or $C_{1-4}$(alky) optionally substituted by halogen;

and n is an integer from 1 to 4; and $R_6$ is hydrogen, halogen, $C_{1-7}$alkyl, $C_{1-4}$alkoxy or trifluoromethyl, Embodiment 2 describes a method in accordance to embodiment 1, wherein the compound of formula (I) is a compound of formula (II)

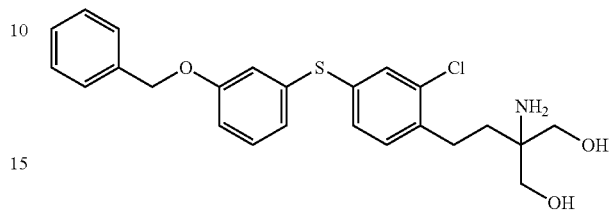

(II)

or a pharmaceutical acceptable salt thereof;

or a phosphate derivative thereof of the following formulae (IIa), (IIb);

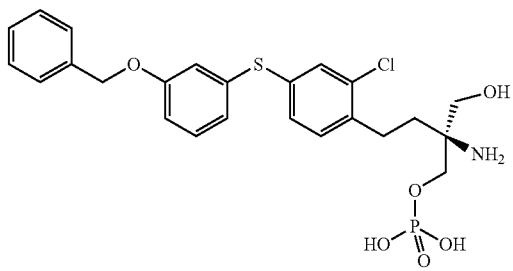

(IIa)

or

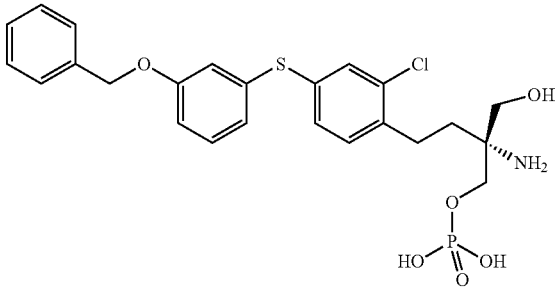

(IIb)

or a pharmaceutically acceptable salt thereof.

Embodiment 3 describes a method in accordance to embodiment 1, wherein the compound of formula (I) is a compound of formula (II)

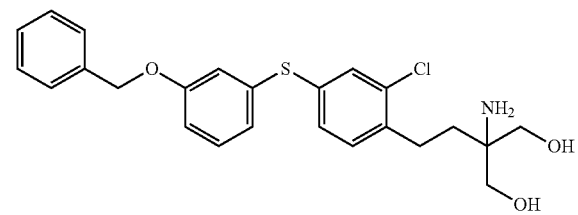

(II)

or a pharmaceutically acceptable salt thereof.

Embodiment 4 describes a compound of formula (I) or a pharmaceutically acceptable salt thereof as defined in embodiment 1 for use m the treatment and/or prevention of GVHD in a patient who was first conditioned as described in embodiment 1 and who then received a hematopoietic stem cell transplantation (HSCT) from a donor.

Embodiment 5 describes a compound for use in accordance to embodiment 4. wherein said compound is a compound of formula (II), (IIa) and/or (IIb) or a pharmaceutically acceptable salt thereof as defined in embodiment 2.

Embodiment 6 describes a method or a compound according to any of the preceding embodiments, e.g. embodiments 1-3, or 4-5, wherein said conditioning is selected from e.g. reduced intensity conditioning (RIC) or myeloablative conditioning:

RIC:

For example Mini-Seattle Conditioning characterized by using fludarabin or another chemotherapeutic agent typically at 30 mg/m2/day for three days followed by total body irradiation (TBS) typically at 1×200 cGy/day, or Myeloablative Conditioning:

Typically high dose chemotherapy and total body irradiation (TBI) is usually performed according to national guidelines adapted to institutional practices, and includes the administration of fludarabin, busulphan, methotrexate, cyclosporin A and cyclophosphamide.

Embodiment 7 describes a method or a compound in accordance to any of the preceding embodiments, e.g. embodiments 1-3, or 4-5, wherein said conditioning is a high chemotherapy comprising one or more agents selected from fludarabin, busulphan, methotrexate, cyclesporin A and cyclophosphamide.

Embodiment 8 describes a method or a compound in accordance to any of the preceding embodiments, e.g. embodiments 1-3, or 4-5, wherein said conditioning is a total body irradiation (TBI) according to national guidelines.

Embodiment 9 describes a method or a compound in accordance to any of the preceding embodiments, e.g. embodiments 1-3, or 4-5, wherein hematopoietic stem cell transplantation (HSCT) is earned out following to conditioning, e.g. immediately after conditioning, or 0-1 day after conditioning, or 1-8 days, or 1-10 days after conditioning.

Embodiment 10 describes a method or a compound in accordance to any of the preceding embodiments, e.g. embodiments 1-3, or 4-5, wherein treatment of the patient with a compound of formula (I) as defined in embodiment 1 is commenced 5 days before conditioning, in particular 3 days before conditioning and especially 1 day before conditioning.

Clinical Study—Description of the Procedure of HSCT:

Population (Eligibility)

The study population (n=approx 10) will comprise the following that have passed screening assessments, comply with inclusion/exclusion criteria, and have provided written consent. Male or female patients must be 18 to 65 years old, inclusive, with a diagnosis that qualify them for a standard allogeneic HSCT where human leukocyte antigen (HLA) matched stem cell source is available. The investigator must ensure that all subjects being considered for the study meet the following eligibility criteria. No additional criteria should foe applied by the investigator, in order that the study population will be representative of all eligible subjects. Subject selection is to be established by checking through all inclusion/exclusion criteria at screening and baseline. A relevant record (e.g. checklist) of the eligibility criteria must be stored with the source documentation at the study site.

Deviation from any entry criterion excludes a subject from enrollment into the study.

Inclusion Criteria

Subjects eligible for inclusion in this study have to fulfill all of the following criteria: Written informed consent must be obtained before any assessment is performed.

1. Patients aged 18 to 65 years, inclusive:
2. Patients must have a hematological malignancy that as per standard medical practice requires myeloablative conditioning (including short term myeloablative reduced intensity conditioning) followed by allogeneic hematopoietic stem cell transplant. Such malignancies include but are not limited to acute myeloid leukemia (AML), acute lymphocytic leukemia (ALL), myelodysplastic syndrome (MDS), chronic lymphocytic leukemia (CLL), marginal zone and follicular lymphomas, large-cell lymphoma, lymphoblastic, Burkitt's and other high grade lymphomas, mantle-cell lymphoma, lymphoplasmacytic lymphoma; prolymphocytic leukemia or multiple myeloma.
3. Recipients must be of good general health defined as having a Kamofsky score ≥60%
4. Suitable stem cell source must be available according to the graft selection algorithm as defined by JACIE* adapted to institutional standards using T-cell replete peripheral stem cells as a graft source. (*JACIE: The Joint Accreditation Committee Europe comprising the International Society for Cellular Therapy & European Group for Blood and Marrow Transplantation)
5. The donor must be 9/10 or 10/10 matched with the recipient using molecular HLA matching techniques.
6. Female and male patients have to fulfill the standard prerequisites for such studies e.g. relating to fertility, pregnancy, sexual activity and the like.
7. Patients must be able to communicate well with the investigator, to understand and to comply with the requirements of the study and to understand and sign the written informed consent.

Exclusion Criteria

Subjects fulfilling any of the following criteria are not eligible for inclusion in this study:

1. Pregnant, planning to get pregnant, and/or lactating females or males planning to father a child within time period of the study or subsequent exclusionary period.
2. Participation in any interventional clinical investigation with an investigational drug within 4 weeks prior to screening or longer if required by local regulations, and for any other limitation of participation based on local regulations.
3. A number of standard cardiovascular conditions:
4. A number of standard pulmonary conditions:
5. Diagnosis or history of macular edema
6. Uncontrolled diabetes mellitus as assessed by the investigator of diabetes complicated with organ involvement such as diabetic nephropathy or retinopathy.
7. Uncontrolled seizure disorder
8. Uncontrolled depression or history of suicide attempts/ideation
9. Untreated or uncontrolled systemic bacterial, viral or fungal infections (including infection with *Aspergillus* or other mold within 30 days) considered active and clinically significant by the investigator
10. Diagnosis of AIDS, Hepatitis B or Hepatitis C infection defined as a positive HIV antibody. Hepatitis 8 surface antigen or Hepatitis C antibody tests, respectively.
11. Herpes simplex virus (HSV) and/or varicella-zoster virus (VZV) immunoglobulin (Ig)G antibody positive patients who, for any reason cannot receive viral prophylaxis treatment (a standard practice for patients undergoing myeloablation and HSCT)

12. Negative for varicella-zoster virus IgG antibodies at Screening.
13. Significant liver disease or liver injury or known history of alcohol abuse, chronic liver or biliary disease
14. Any of the following abnormal laboratory values:
    a. serum creatinine greater than 2.0 mg/dL (176 μmol/L)
    b. AST or ALT or ALP greater than 5 times upper limit of normal
15. Active non-hematologic malignancy within 5 years with the exception of successfully treated basal cell carcinoma.
16. Any medical condition, as assessed by the primary treating physician that is unstable or may jeopardize the patient in any way in case of participation in the study.
17. Any drag required that is not compatible with a compound of the invention
18. Prior use of alemtuzumab (Campath) or anti-thymocyte globulin (ATG) within 3 months.
19. Have received any live or live attenuated vaccines (including for varicella-zoster virus or measles) within 2 months prior to initiating treatment with a compound of the invention.
20. Prior myeloablative allogeneic transplant
21. Recipients of cord blood or haploidentical transplant
22. Recipient of a solid organ transplant
23. History of hypersensitivity to the study drug or to drugs with similar chemical structures as a compound of formula (I). No additional exclusions may be applied by the investigator, in order to ensure that the study population will be representative of all eligible patients.

Treatment Procedure

1. Drug for treating GVHD

The drug, a compound of formula (I), in particular a compound of formula (II), especially capsules comprising 1, 2, 3 or 5 mg of 2-amino-2-[4-(3-benzyloxyphenylthio)-2-chlorophenyl]ethyl-propane-1,3-diol or a pharmaceutically acceptable salt thereof are provided.

The treatment typically comprises:

A: A screening period (Days −50 to −2), Baseline (Day −1),

8: Drug treatment period from Day 1 to Day 111 and a follow-up period up to 365 days (from transplant), wherein the drug is a compound of formula (I) or a pharmaceutically acceptable salt thereof.

C: Myeloablative conditioning will be performed between Day 2 and Day 10 as per standard of care using chemotherapy (e.g. fludarabin, busulphan, cyclophosphamide, methotrexate) with total body irradiation (TBI, see below).

D: Transplantation (infusion of stem cells), i.e. HSCT will be performed on Day 11. Standard activities, in addition to the investigative treatment may include standard GVHD prophylaxis, pre and post transplant supportive care and follow-up assessments according to the institutional practices.

2. Treatment Arms

Patients will be assigned to the following treatment:

Single arm: 2-amino-2-[4-(3-benzyloxyphenylthio)-2-chlorophenyl]ethyl-propane-1,3-diol, 3 mg once daily for 111 days 3. Treatment assignment Subject numbers will be assigned in ascending, sequential order to eligible subjects (see below for details).

4. Treatment blinding

This is an open-label study and all subjects will receive the same treatment.

5. Subject screening Numbering

Each subject screened is assigned a unique screening number.

6. Dispensing the study treatment

Appropriate documentation of the subject specific dispensing process must be maintained. The study drug for the subjects will be dispensed and supplied by the sponsor of the study. Medication labels will comply with legal requirements of the country where the study is performed and be printed in the local language. Storage conditions for the study drug will be included on the medication label.

7. Instructions for prescribing and taking study treatment

During the hospitalization period study mediation will be administered by the study center personnel with approximately 180-240 ml of water. The dispensation of the study medication must be carefully supervised and controlled. All dosages prescribed and diseased to the subject and all dose changes during the study must be recorded on the Dosage Administration Record CRF (CRF=company for clinical readout assessment).

8. Permitted dose adjustments and interruptions of study treatment

Study drug dose adjustments may be permitted and drug interruptions will be allowed based on the judgment of the Investigator. Conditions/events that may lead to the study drug interruptions based on investigator judgment and overall clinical assessment include:

reported serious, adverse event emergency medical condition with or without involving use of excluded concomitant medications clinically significant laboratory value(s) or abnormal test or examination result(s)

patient's non-compliance

In order to avoid a negative impact of study drug discontinuation and re-start on patient's safety, a discussion between the investigator and sponsor will take place on a case by case basis. This is to decide whether or not to continue treatment considering the reason for, timing and duration of discontinuation. This is also to determine whether additional safety measures are required or not when re-starting study drug, e.g. if the interruption was long enough to warrant cardiac monitoring. In case of notable adverse events, safety concerns and/or based on pharmacokinetic data during the study, administration of a dose below the planned dose, i.e 3 mg per day may be considered. For patients who are unable to tolerate the protocol-specified dosing scheme, dose adjustments and interruptions are permitted in order to keep the patient on study drug. These changes must be recorded on the Dosage Administration Record CRF.

Concomitant Treatment

All prescription medications, over-the-counter drugs and significant non-drug therapies (including physical therapy and blood transfusions) administered or taken within the timeframe defined in the entry criteria prior to the start of the study and during the study, must be recorded on the Concomitant medications/Significant non-drug therapies section of the CRF. Medication entries should be specific to trade name, the single dose and unit, the frequency and route of administration, the start and discontinuation date and the reason for therapy. Currently, there is no uniform protocol for the use of conditioning, GVHD propylaxis, HSCT and overall peritransplant care, any or all of which may vary significantly across different sites and may also vary patient by patient at the same site. Therefore, such concomitant treatments will be used according to institutional practices.

The following concomitant treatments) is (are) typically available in the event of a need:

Potent CYP3A4 inhibitors, e.g. selected from Atazanavir, Indinavir, Nelfinavir, Ritonavir, Saquinavir, Amiodarone, Cimetidine, Clarithromycin, Ciprofloxacin, Diltiazem, Erythromycin, Fluvoxamine and the like. This Potent CYP3A4 inhibitors may be administered to patients as standard of care. In order to mitigate the risk for potential drug-drug interactions with the treatment drug, PK samples will be analyzed on an ongoing basis.

Conditioning of a Patient

Reduced Intensity Conditioning:

As an example, Mini-Seattle Conditioning with Fludarabin will be used at 30 mg/m2/day for three days followed by total body irradiation (TBI) (1×200cGy/day)

Myeloablative Conditioning

High dose chemotherapy and total body irradiation (TBI) will be performed according to national guidelines adapted to institutional practices, and may include the use of fludarabin, busulphan, methotrexate, cyclosporin A and cyclophosphamide. The following dosing regimens are given as examples:

1) Fludarabin at 25 mg/m2/day IV×3 days (for approximately 2-3 days) for a total dose of 75 mg/m2.

2) Busulphan at 0.8 mg/kg/6 h (for approximately 2 to 4 days)

3) Cyclophosphamide at 60 mg/kg/day IV×2 days (approximately for 2 days) for a total dose of 120 mg/kg. To reduce the risk CYC-induced hemorrhagic cystitis, patients will also receive high volume fluid flushes and mesna.

4) TBI will occur from approximately days 8 to 10 (days −8 and −1 relative to HSCT). The recommended TBI dose is 200 cGy given twice daily for a total dose of 1200 cGy.

Prophylaxis for GVHD

Usually, a compound of formula (I) will be given as an add-on-treatment to the normal treatment drug given to patients to prevent GVHD. The standard of care for prophylaxis of GVHD has many side effects and in a high percentage of patients does not prevent GVHD.

Accordingly, patients may receive prophylaxis as per institutional practices using for example cyclosporin A (CsA): mycophenolate or methotrexate. As an example, patients begin CsA on Day 8 (day −3 relative to HSCT) at an initial dose of 2.5 mg/kg IV over 2 hours every 12 hours. Dose adjustments may be made on the basis of toxicity and CsA levels with a targeted trough level of 150-400 mg/L. Once a patient can tolerate oral medications, CsA is typically converted to an per oral (p.o.) form. Initial p.o. dosing might be the current intra venous (i.v.) dose given twice daily. CsA dosing is typically monitored at least weekly and may be altered as clinically appropriate.

Methotrexate schedule and dosing may be adapted according to internal standards of an institution (e.g. 10 mg/kg on Day 11, 6 mg/kg on Day 13 and on Day 16). Mycophenotale may typically be given according to the institutional practices (e.g. 2×100 mg per day after mini-Seattle conditioning). Dose adjustments may be made based or clinical side effects.

Hematopoetic Stem Cell Transplant (HSCT)

Peripheral mobilized stem cell will be used according to institutional practices.

Suitable stem cell source must be available according to the graft selection algorithm as defined by JACIE* adapted to institutional standards using T-cell replete peripheral stem cells as a graft source. (*JACIE: The Joint Accreditation Committee Europe comprising the international Society for Cellular Therapy & European Group for Blood and Marrow Transplantation). In addition, the donor must be 9/10 or 10/10 matched with the recipient using molecular HLA matching techniques.

We performed lethal GvHD in mice according to a previous report described in Transplantation 11(4) (1971): 378-382.

Female BALB/cAnNCrj mice and female Crj:BDF1 mice were purchased from CHARLES RIVER JAPAN and used at 10 weeks of age as donors and recipients, respectively.

Spleens were collected from donor BALB/c mice. The spleens were placed in a RPMI-1640 medium (GIBCO) and were gently pressed two slide glasses to make a single cell suspension. The single cell suspension was passed through a cell strainer (70 um, FALCON). The filtrate was centrifuged to collect the cell pellet. The pellet was re-suspended in RPMI-1640 medium. The number of nucleated cells in the suspension was calculated by staining using Turk's solution. The suspension was diluted appropriately with RPMI-1640 medium to finally make a suspension of $2 \times 10^8$ cells/mL. This suspension served as a splenic cell suspension.

Recipient BDF1 mice were treated with a dose of cyclophosphamide (SHIONOGI & CO., LTD.) at 300 mg/kg intraperitoneally on day0. One day after cyclophosphamide treatment, the BDF1 mice were intravenously injected with 0.25 mL ($5 \times 10^7$ cells/mouse) of the splenic cell suspension from BALB/c mice to induce lethal GvHD.

Treatment with a Compound (Control/CsA/KRP203)

The compounds were orally administrated once a day from day 1 (just after injection of the splenic cells) to day 20. The mice were observed until day 70.

The results are shown in table 1. Cyclosporin A suppressed lethal GVHD in mice. However onset of lethal GVHD was observed upon withdrawal of cyclosporin A (treatment stop at day 20). KRP-203 at 0.03 mg/kg, p.o. fully prevented lethal GVHD in mice. KRP-203 showed sustained efficacy after discontinuation of treatment (in contrast to cyclosporin A).

TABLE 1

Effects of KRP-203 and cyclosporin A (CsA) on lethal GvHD in mice (treatment up to day 20)

| Compounds | No. of mice | % Survival Days after injection of the splenic cells | | | | | | | | |
|---|---|---|---|---|---|---|---|---|---|---|
| | | Day 5 | 8 | 10 | 12 | 20 | 25 | 30 | 40 | 70 |
| Control | 9 | 100% | 44% | 0% | 0% | 0% | 0% | 0% | 0% | 0% |
| CsA 25 mg/kg | 8 | 100% | 100% | 100% | 100% | 100% | 88% | 75% | 25% | 25% |

TABLE 1-continued

Effects of KRP-203 and cyclosporin A (CsA) on lethal GvHD in mice (treatment up to day 20)

| Compounds | No. of mice | % Survival Days after injection of the splenic cells | | | | | | | | |
|---|---|---|---|---|---|---|---|---|---|---|
| | | Day 5 | 8 | 10 | 12 | 20 | 25 | 30 | 40 | 70 |
| KRP-203 0.01 mg/kg | 9 | 100% | 89% | 67% | 44% | 44% | 44% | 44% | 33% | 33% |
| KRP-203 0.03 mg/kg | 9 | 100% | 100% | 100% | 100% | 100% | 100% | 100% | 100% | 100% |
| KRP-203 0.1 mg/kg | 9 | 100% | 100% | 100% | 100% | 100% | 100% | 100% | 100% | 100% |
| KRP-203 0.3 mg/kg | 9 | 100% | 100% | 100% | 100% | 100% | 100% | 100% | 100% | 100% |
| KRP-203 1 mg/kg | 9 | 100% | 100% | 100% | 100% | 100% | 100% | 100% | 100% | 100% |

The invention claimed is:

1. A method of preventing acute graft versus host disease, comprising:

administering to a patient suffering from a hematological malignancy selected from: acute myeloid leukemia (AML), acute lymphocytic leukemia (ALL), myelodysplastic syndrome (MDS), chronic lymphocytic leukemia (CLL), marginal zone and follicular lymphomas, large-cell lymphoma, Burkitt's lymphomas, mantle-cell lymphoma, lymphoplasmacytic lymphoma, prolymphocytic leukemia and multiple myeloma, who is undergoing hematopoietic stem cell transplantation and is at risk of acute graft versus host disease and in need thereof an effective amount of a compound selected from the group consisting of:

formula (II) or a pharmaceutically acceptable salt thereof, formula (IIa) or a pharmaceutically acceptable salt thereof, and formula (IIb) or a pharmaceutically acceptable salt thereof;

conditioning said patient such that all bone marrow and the immune system are substantially destroyed; and transplanting hematopoietic stem cells from a donor to said patient, wherein the compound of formula (II) is:

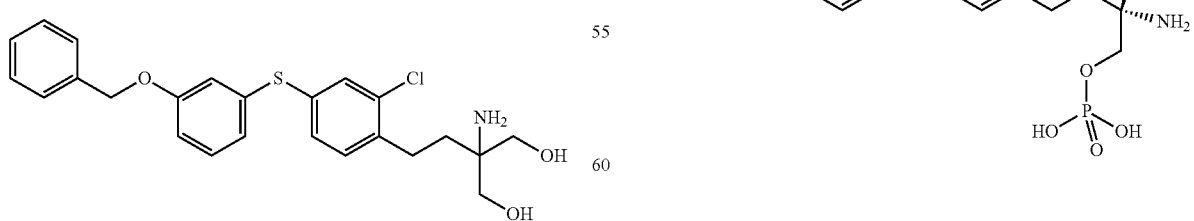

(II)

or a pharmaceutically acceptable salt thereof, wherein the compound of formula (IIa) is, (IIa)

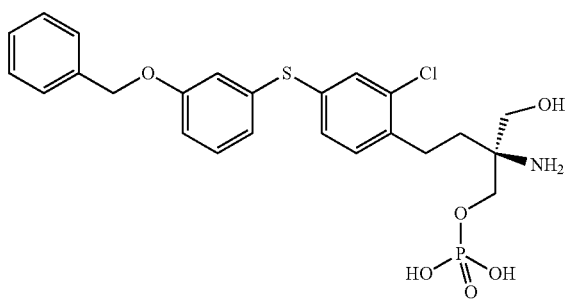

or a pharmaceutically acceptable salt thereof, wherein the compound of formula (IIb) is, (IIb)

or a pharmaceutically acceptable salt thereof.

2. The method of claim 1, wherein the compound administered to the patient is a compound of formula (II):

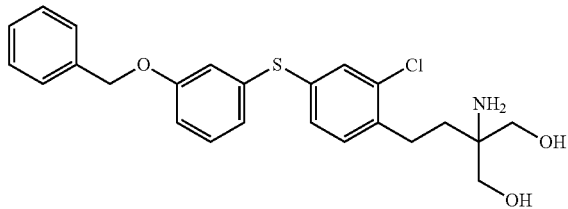

or a pharmaceutically acceptable salt thereof.

3. The method of claim 1, wherein said conditioning is one of Reduced Intensity Conditioning and Myeloablative Conditioning.

4. The method of claim 1, wherein said conditioning is a high dose chemotherapy comprising at least one agent selected from the group consisting of fludarabin, busulphan, methotrexate, cyclosporin A and cyclophosphamide.

5. The method of claim 1, wherein said conditioning is a total body irradiation according to national guidelines.

6. The method of claim 1, wherein the hematopoietic stem cell transplantation is carried out immediately after the conditioning, 0-1 day after the conditioning, 1-8 days after the conditioning, or 1-10 days after the conditioning.

7. The method of claim 1, wherein the treating of the patient with the compound of formula (II), (IIa) or (IIb), or a pharmaceutically acceptable salt thereof is commenced 5 days before the conditioning, 3 days before the conditioning or 1 day before the conditioning.

8. The method of claim 2, wherein said conditioning is one of Reduced Intensity Conditioning and Myeloablative Conditioning.

9. The method of claim 2, wherein said conditioning is a high dose chemotherapy comprising at least one agent selected from the group consisting of fludarabin, busulphan, methotrexate, cyclosporin A and cyclophosphamide.

10. The method of claim 2, wherein said conditioning is a total body irradiation according to national guidelines.

11. The method of claim 2, wherein the hematopoietic stem cell transplantation is carried out immediately after the conditioning, 0-1 day after the conditioning, 1-8 days after the conditioning, or 1-10 days after the conditioning.

12. The method of claim 2, wherein the treating of the patient with the compound of formula (II), or a pharmaceutically acceptable salt thereof is commenced 5 days before the conditioning, 3 days before the conditioning or 1 day before the conditioning.

13. The method of claim 1, wherein the effective amount of a compound of formula (II) or a pharmaceutically acceptable salt thereof is a 3 mg oral daily dosage.

14. The method of claim 1, wherein the patient suffers from acute myeloid leukemia (AML) and wherein the effective amount of a compound of formula (II) or a pharmaceutically acceptable salt thereof is a 3 mg oral daily dosage.

15. The method of claim 1, wherein the compound of formula (II), or a pharmaceutically acceptable salt thereof, is co-administered with cyclosporin A (CsA), mycophenolate or methotrexate.

16. The method of claim 1, wherein the patient suffers from acute myeloid leukemia (AML), wherein the effective amount of a compound of formula (II) or a pharmaceutically acceptable salt thereof is a 3 mg oral daily dosage; and
wherein the compound of formula (II), or a pharmaceutically acceptable salt thereof, is co-administered with cyclosporin A (CsA).

* * * * *